(12) United States Patent
Schlosser et al.

(10) Patent No.: US 9,861,103 B2
(45) Date of Patent: Jan. 9, 2018

(54) COMBINATION OF PETHOXAMID AND PICLORAM

(71) Applicant: CHEMINOVA A/S, Harboøre (DK)

(72) Inventors: Henrik Gronnegaard Schlosser, Lemvig (DK); Barrie Hunt, Lincolnshire (GB); Harald B. Teicher, Thyborøn (DK)

(73) Assignee: CHEMINOVA A/S, Harboøre (DK)

( * ) Notice: Subject to any disclaimer, the term of this patent is extended or adjusted under 35 U.S.C. 154(b) by 0 days.

(21) Appl. No.: 14/899,716

(22) PCT Filed: Jun. 19, 2014

(86) PCT No.: PCT/DK2014/050176
§ 371 (c)(1),
(2) Date: Dec. 18, 2015

(87) PCT Pub. No.: WO2014/202092
PCT Pub. Date: Dec. 24, 2014

(65) Prior Publication Data
US 2016/0143281 A1    May 26, 2016

(30) Foreign Application Priority Data

Jun. 20, 2013 (EP) .................................. 13172999

(51) Int. Cl.
*A01N 37/20* (2006.01)
*A01N 43/40* (2006.01)
*A01N 37/18* (2006.01)

(52) U.S. Cl.
CPC ............ *A01N 43/40* (2013.01); *A01N 37/18* (2013.01); *A01N 37/20* (2013.01)

(58) Field of Classification Search
CPC combination set(s) only.
See application file for complete search history.

(56) References Cited

U.S. PATENT DOCUMENTS

2011/0059849 A1*  3/2011  Refardt ............... A01N 43/80
                                                                      504/138

FOREIGN PATENT DOCUMENTS

| EP | 0206251 A1 | 12/1986 |
|---|---|---|
| WO | WO-02100171 A1 | 12/2002 |
| WO | WO-2009115433 A2 | 9/2009 |
| WO | WO-2009153247 A2 | 12/2009 |

OTHER PUBLICATIONS

HCAPLUS Abstract 2002:88809 (2002).*
Pesticide Manual, 15th edition, BCPC, pp. 905-908 (2009).*
EPA R.E.D. Facts (Picloram), pp. 1-11 (1995).*
International Search Report for PCT/DK2014/050176, ISA/EP, Rijswijk; dated Aug. 13, 2014.

* cited by examiner

*Primary Examiner* — John Pak
(74) *Attorney, Agent, or Firm* — Harness, Dickey & Pierce, P.L.C.

(57) ABSTRACT

Presented is a composition comprising pethoxamid and picloram. The composition exerts asynergistical effect.

11 Claims, No Drawings

COMBINATION OF PETHOXAMID AND PICLORAM

The present invention relates to herbicidally active compositions comprising pethoxamid and picloram as well as agriculturally acceptable derivatives thereof

BACKGROUND

In the case of crop protection compositions, it is desirable in principle to increase the specific activity of an active compound and the reliability of the effect. It is particularly desirable for the crop protection composition to control the harmful plants effectively, but at the same time to be compatible with the useful plants in question. Also desirable is a broad spectrum of activity allowing the simultaneous control of harmful plants. Frequently, this cannot be achieved using a single herbicidally active compound.

With many highly effective herbicides, there is the problem that their compatibility with useful plants, in particular dicotyledonous crop plants, such as cotton, oilseed rape and graminaceous plants, such as barley, millet, corn, rice, wheat and sugar cane, is not always satisfactory, i.e. in addition to the harmful plants, the crop plants, too, are damaged on a scale which cannot be tolerated. By reducing the application rates, the useful plants are spared; however, naturally, the extent of the control of harmful plants decreases, too.

In addition there is frequently the problem that, in order to achieve the desired herbicidal activity, the herbicides can only be used within a narrow time frame, where the time frame can be influenced unpredictably by weather conditions.

It is known that special combinations of different specifically active herbicides result in enhanced activity of a herbicide component in the sense of a synergistic effect. In this manner, it is possible to reduce the application rates of herbicidally active compounds required for controlling the harmful plants.

Furthermore, it is known that in some cases joint application of specifically acting herbicides with organic active compounds, some of which may also have herbicidal activity, allows better crop plant compatibility to be achieved. In these cases, the active compounds act as antidotes or antagonists and are also referred to as safeners, since they reduce or even prevent damage to the crop plants.

The herbicidal active compound pethoxamid is known from European patent application no. EP 206251-A1 and is generally used to control weeds in various crops such as control of grass weeds and broad-leaved weeds. The compound picloram is a plant growth regulator and known from.

It is an object of the present invention to provide herbicidal compositions which are highly active against unwanted harmful plants. At the same time, the compositions should have good compatibility with useful plants. In certain aspects of the invention, the compositions according to the invention have a broad spectrum of activity.

DESCRIPTION OF THE INVENTION

The present invention relates to a herbicidal composition for weed control comprising a synergistically effective amount of the combination of, as component A) pethoxamid and, as component B) picloram and agriculturally acceptable derivatives thereof, and to a method of controlling weeds with said combination. The method comprises exposing the harmful plants to a synergistically effective amount of a combination of, as component A) pethoxamid and, as component B) picloram and agriculturally acceptable derivatives thereof.

Accordingly, the present invention relates to herbicidally active compositions comprising:

As component A, pethoxamid and as component B, picloram and agriculturally acceptable derivatives thereof.

The invention relates in particular to compositions in the form of herbicidally active crop protection compositions comprising as component A, a herbicidally effective amount of pethoxamid and picloram and its salts and esters as component B, and also at least one liquid and/or solid carrier and/or one or more surfactants and, if desired, one or more further auxiliaries customary for crop protection compositions.

The invention also relates to compositions in the form of a crop protection composition formulated as a 1-component composition comprising an active compound combination comprising pethoxamid and picloram and agriculturally acceptable derivatives thereof, and at least one solid or liquid carrier and/or one or more surfactants and, if desired, one or more further auxiliaries customary for crop protection compositions.

The invention also relates to compositions in the form of a crop protection composition formulated as a 2-component composition comprising a component that is pethoxamid, a solid or liquid carrier and/or one or more surfactants, and a second component comprising picloram and agriculturally acceptable derivatives thereof, a solid or liquid carrier and/or one or more surfactants, where additionally both components may also comprise further auxiliaries customary for crop protection compositions.

Surprisingly, the compositions according to the invention have better herbicidal activity, i.e. better activity against harmful plants, than would have been expected based on the herbicidal activity observed for the individual compounds. The herbicidal activity to be expected for mixtures based on the individual compound can be calculated using Colby's formula. If the activity observed exceeds the expected additive activity of the individual compounds, synergism is said to be present. In an aspect of the invention the composition has broader activity spectrum, i.e. a herbicidal activity towards a diverse group of harmful plants.

In addition, the compositions according to the invention extend the time frame during which the desired herbicidal action can be achieved. This allows a more flexible use over time of the compositions according to the invention compared to the individual compounds.

The invention furthermore relates to a method for controlling unwanted vegetation by application of a composition as herein described, in particular where crop plants are cultivated, for example in crops of the following crop plants: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana*

*tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor* (s. *vulgare*), *Theobroma cacao, Trifolium pratense, Triticum aestivum, Triticale, Triticum durum, Vicia faba, Vitis vinifera, Zea mays*, especially crops of cereals, corn, soybeans, rice, oilseed rape, cotton, potatoes, peanuts, sunflower or permanent crops, and also in crops which are resistant to one or more herbicides or to attack by insects owing to genetic engineering or breeding.

The assignment of the active compounds to the respective mechanisms of action is based on current knowledge. If several mechanisms of action apply to one active compound, this substance was only assigned to one mechanism of action.

Since picloram comprises ionizable functional groups i.e. a carboxylic acid and amine group, it can also be employed, in part or in total, in the form of agriculturally acceptable derivatives thereof. An "agriculturally acceptable derivative", when used to describe the carboxylic acid functionality of picloram, is defined as any salt, ester, acylhydrazide, imidate, thioimidate, amidine, amide, orthoester, acylcyanide, acyl halide, thioester, thioester, dithiolester, nitrile or any other acid derivative well known in the art which (a) does not substantially affect the herbicidal activity of picloram, and (b) is or can be hydrolyzed in plants or soil to the free carboxylic acid that, depending upon the pH, is in the dissociated or the undissociated form. Likewise, an "agriculturally acceptable derivative", when used to describe the amine functionality of picloram, is defined as any salt, silylamine, phosphorylamine, phosphinimine, phosphoramidate, sulfonamide, sulfinimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of picloram, and (b) is or can be hydrolyzed in plants or soil to a free amine. Mixtures of these derivatives may also be employed.

Preferred are, in general, esters and the salts of those cations and the acid addition salts of those acids whose cations and anions, respectively, have no adverse effect on the activity of the active compound.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methyl ammonium, isopropylammonium, dimethylammonium, diisopropylammonium, trimethylammonium, tetramethylammonium, tetraethylammonium, tetrabutylammonium, 2-hydroxyethyl-ammonium, 2-(2-hydroxyeth-1-oxy)eth-1-ylammonium, di(2-hydroxyeth-1-yl)-ammonium, benzyltrimethyl-ammonium, benzyltriethyl-ammonium, furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl) sulfoxonium.

Anions of useful acid addition salts are primarily chloride, bromide, fluoride, iodide, hydrogensulphate, methylsulphate, sulphate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Suitable esters include those derived from $C_1$-$C_{12}$-alkyl, $C_3$-$C_{12}$-alkenyl or $C_3$-$C_{12}$-alkynyl alcohols, such as methanol, iso-propanol, butanol, 2-ethylhexanol, octanol, butoxyethanol, methoxypropanol, allyl alcohol, propargyl alcohol or cyclohexanol Preferred picloram derivatives are salts and esters and include the dimethylammonium-salt, the triethylammonium salt, the triisopropanolammonium salt, the isoctyl ester (isooctyl) and the potassium salt; as well as mixtures of these.

In compositions comprising pethoxamid (component A) and picloram and agriculturally acceptable derivatives thereof (component B), the weight ratio of the active compounds A:B is generally in the range of from 1:1 to 500:1, preferably in the range of from 1:1 to 250:1, in particular in the range of from 1:1 to 150:1, particularly preferably in the range of from 1:1 to 100:1, most preferably 2:1 to 70:1; even more preferably between 10:1 to 70:1 and utmost preferably between 20:1 to 65:1. Same ratios are useful for use in the methods herein described.

Additionally, herbicides different from pethoxamid and picloram may also be added to the combination. The optional additional herbicides can advantageously be included for example to widen the spectrum of action or to prevent build-up of resistance. Suitable examples of such herbicides are e.g. from group c1-c15:

c1) from the group of the lipid biosynthesis inhibitors:
ACC herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, as well as non ACC herbicides such as benfuresate, butylate, cycloate, dalapon, dimepiperate, EPIC, esprocarb, ethofumesate, flupropanate, molinate, orbencarb, pebulate, prosulfocarb, TCA, thiobencarb, tiocarbazil, triallate and vernolate;

c2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, mesosulfuron, metsulfuron, metsulfuron-methyl, nicosulfuron, orthosulfamuron, oxasulfuron, primisulfuron, primisulfuron-methyl, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, trib enuron, tribenuron-methyl, trifloxysulfuron, triflusulfuron, triflusulfuron-methyl and tritosulfuron; imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam;

pyrimdinylbenzoates such as bispyribac, bispyribac-sodium, pyribenzoxim, pyriftalid, pyriminobac, pyriminobac-methyl, pyrithiobac, pyrithiobac-sodium, and also sulfonylaminocarbonyltriazolinone herbicides such as flucarbazone, flucarbazone-sodium, propoxycarbazone, propoxycarbazone-sodium, thiencarbazone and thiencarbazone-methyl. Among these, compositions comprising at least one imidazolinone herbicide represent a preferred embodiment of the invention;

c3) from the group of the photosynthesis inhibitors:
amicarbazone, photosystem II inhibitors, for example, triazine herbicides, including chlorotriazines, triazinones, triazinediones, methylthiotriazines; and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazine, terbutryn and trietazine; arylureas such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thidiazuron; phenyl carbamates such as desmedipham, karbutilate, phenmedipham, phenmedipham-ethyl; nitrile herbicides such as bromofenoxim, bromoxynil and its salts and esters, ioxynil and its salts and esters; uracils such as bromacil, lenacil and terbacil; as well as bentazone and bentazone-sodium, pyridate, pyridafol, pentanochlor and propanil; and photosystems I inhibitors such as diquat, diquat-dibromide, paraquat, paraquat-dichloride and paraquat-dimetilsulphate.

c4) from the group of the protoporphyrinogen-IX oxidase inhibitors: acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, sulfentrazone, thidiazimin, saflufenacil;

c5) from the group of the bleacher herbicides:
PDS-inhibitors: beflubutamid, diflufenican, fluridone, fluorochloridone, flurtamone, norflurazon, and picolinafen; HPPD-inhibitors: benzobicyclon, benzocenap, isoxaflutole, mesotrione, pyrasulfotole, pyrazolynate, pyrazoxyfen, sulcotrione, tefuryltrione, tembotrione, topramezone, bicyclopyrone; bleachers; unknown target: aclonifen, amitrol and clomazone;

c6) from the group of the EPSP synthase inhibitors:
glyphosate, glyphosate-isopropylammonium and glyphosate-trimesium (sulfosate), glyphosate-potassium; glyphosate-sodium, glyphosate-ammonium;

c7) from the group of the glutamine synthase inhibitors:
bilanaphos (bialaphos), bilanaphos-sodium, glufosinate and glufosinate-ammonium;

c8) from the group of the DHP synthase inhibitors:
asulam;

c9) from the group of the mitosis inhibitors:
compounds of group K1: dinitroanilines, such as benfluralin, butralin, dinitramine, ethalfluralin, fluchloralin, oryzalin, pendimethalin, prodiamine and trifluralin; phosphoramidates, such as amiprophos, amiprophos-methyl and butamiphos; benzoic acids, such as chlorthal, chlorthal-dimethyl; pyridines, such as dithiopyr and thiazopyr; benzamides, such as propyzamide and tebutam; compounds of group K2: chlorpropham, propham and carbetamide.

c10) from the group of the VLCFA inhibitors:
chloroacetamides such as acetochlor, alachlor, butachlor, dimethachlor, dimethanamid, dimethenamid-P, metazachlor, metolachlor, metolachlor-S, pretilachlor, propachlor, propisochlor and thenylchlor;
Oxyacetanilides, such as flufenacet and mefenacet; acetanilides, such as diphenamid, naproanilide and napropamide, tetrazolinones, such as fentrazamide, and
others, such as anilofos, cafenstrol, piperophos and pyroxasulfone. From among the VLCFA inhibitors, preference is given to chloroacetamides, oxyacetamides and pyroxasulfone;

c11) from the group of the cellulose biosynthesis inhibitors:
chlorthiamid, dichlobenil, flupoxam and isoxaben;

c12) from the group of the decoupler herbicides:
dinoseb, dinoterb and DNOC and its salts;

c13) from the group of the auxin herbicides:
2,4-D and its salts and esters, 2,4-DB and its salts and esters, aminopyralid and its salts such as aminopyralid-tris (2-hydroxypropyl)ammonium and its esters, benazolin, benazolin-ethyl, chioramben and its salts and esters, clomeprop, dicamba and its salts and esters, dichlorprop and its salts and esters, dichlorprop-P and its salts and esters, MCPA and its salts and esters, MCPA-thioethyl, MCPB and its salts and esters, mecoprop and its salts and esters, mecoprop-P and its salts and esters, quinclorac, quinmerac, TBA (2,3,6) and its salts and esters, and aminocyclopyrachlor and its salts and esters, esters and salts of clopyralid, fluroxypyr and triclopyr;

c14) from the group of the auxin transport inhibitors:
diflufenzopyr, diflufenzopyr-sodium, naptalam and naptalam-sodium;

c15) from the group of the other herbicides: bromobutide, chlorflurenol, chlorflurenol-methyl, cinmethylin, cumyluron, dalapon, dazomet, difenzoquat, difenzoquat-metilsulphate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, and tridiphane.

Additional, safeners may also be added to the composition, suitable safeners are e.g.: benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4,5]decane (AD 67, CAS nr. 71526-07-3), 4-carboxy-3,4-dihydro-2H-1-benzopyran-4-acetic acid (CL 304,415, CAS nr. 31541-57-8), 2,2-dichloro-N-[2-oxo-2-(2-propenylamino)ethyl]-N-2-propenylacetamide (DKA-24, CAS nr. 97454-00-7), 2-dichloromethyl-2-methyl-1,3-dioxolane (MG 191, CAS nr. 22052-63-7), 3-(dichloroacetyl)-2,2,5-trimethyl-1,3-oxazolidine (RD 29148, CAS nr. 52836-31-4), and 1-dichloroacetylazepane (TI-35, CAS nr. 64661-12-7).

In an embodiment of the present invention, A) picloram and B) pethoxamid are the sole active herbicidal/pesticidal compounds applied in the methods herein described and/or present in the compositions as herein described and the use thereof. Accordingly, one aspect of the invention relates to a herbicidal method and/or composition for weed control containing a synergistically effective amount of the combination of, as component A) pethoxamid and, as component B) picloram, with components A and B being the only herbicidal/pesticidal active compounds present and/or used in the application methods herein described.

The compositions according to the invention are suitable as herbicides. They are suitable such or as an appropriately formulated composition. The compositions according to the invention control vegetation on non-crop areas very efficiently, especially at high rates of application. They act against broad-leafed weeds and grass weeds in crops such as cereals (e.g. wheat and rice), oilseed rape, corn, soybeans and cotton without causing any significant damage to the crop plants.

In addition, the compositions according to the invention may also be used in crops which tolerate the action of herbicides owing to breeding, including genetic engineering methods.

In addition, the compositions according to the invention can also be used in crops which tolerate insects or fungal attack as the result of breeding, including genetic engineering methods.

The compositions according to the invention or the crop protection compositions comprising them or formulated therefrom can be used, for example, in the form of ready-to-use solutions, emulsifiable concentrates, emulsions, suspensions, wettable powders, soluble powders, granules, soluble granules, dispersible granules, microemulsions, microcapsule suspensions and mixtures thereof, by means of spraying, atomizing, dusting, broadcasting or watering. The use forms depend on the intended purpose; in any case, they should ensure the finest possible distribution of the active compounds according to the invention.

The crop protection compositions comprise a herbicidally effective amount of the composition according to the invention, i.e. pethoxamid and picloram and agriculturally acceptable derivatives thereof, and also auxiliaries customary for formulating crop protection agents.

Examples of auxiliaries customary for the formulation of crop protection agents are inert auxiliaries, solid or liquid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R. T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are in particular liquid or solid carriers. Examples of liquid carriers are: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, for example amines such as N-methylpyrrolidone, and water. Solid carriers are for example mineral earths such as silicas, silica gels, silicates, talc, kaolin, limestone, lime, chalk, bole, loess, clay, dolomite, diatomaceous earth, calcium sulphate, magnesium sulphate and magnesium oxide, ground synthetic materials, fertilizers such as ammonium sulphate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulphates, lauryl ether sulphates and fatty alcohol sulphates, and salts of sulphated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or grinding the active ingredients together with a solid carrier.

Granules, for example coated granules, impregnated granules and homogeneous granules; can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the active components, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the active compounds in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

Particularly preferred formulations will be made up as follows: (throughout, percentages are by weight):

| Emulsifiable concentrates: | |
|---|---|
| Component A and component B: | 1 to 99%, preferably 60 to 90% |
| Surfactant: | 1 to 30%, preferably 1 to 20% |
| Solvent: | 1 to 80%, preferably 1 to 35% |

| Dusts: | |
|---|---|
| Component A and component B: | 0.1 to 99%, preferably 1 to 80% |
| Solid carrier: | 1 to 99.9%, preferably 15 to 90% |

| Suspension concentrates: | |
|---|---|
| Component A and component B: | 5 to 75%, preferably 10 to 50% |
| Water: | 94 to 24%, preferably 88 to 30% |
| Surfactant: | 1 to 40%, preferably 2 to 30% |

| Suspo-emulsion | |
|---|---|
| Component A and component B: | 1 to 99%, preferably 10 to 50% |
| Surfactant: | 1 to 30%, preferably 1 to 20% |
| Solvent | 1 to 80%, preferably 1 to 35% |

| Wettable powders: | |
|---|---|
| Component A and component B: | 0.1 to 90%, preferably 1 to 80% |
| Surfactant: | 1 to 50%, preferably 1 to 15% |
| Solid carrier: | 1 to 95%, preferably 15 to 90% |

| Granulates: | |
|---|---|
| Component A and component B: | 0.1 to 90%, preferably 1 to 80% |
| Surfactant: | 1 to 50%, preferably 1 to 15% |
| Solid carrier: | 1 to 95%, preferably 15 to 90% |

The compositions of the invention can for example be formulated as follows:
1. Products for Dilution with Water.
A) Water-Soluble Concentrates (SL, LS)
   10 parts by weight of the active compound(s) are dissolved in 90 parts by weight of water or a water-soluble solvent. As an alternative, wetters or other auxiliaries are added. The active compound(s) dissolve(s) upon dilution with water, whereby a formulation with 10% (w/w) of active compound(s) is obtained.

B) Dispersible Concentrates (DC)
   20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)
   15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)
   25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)
   In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)
   50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)
   75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF) In an agitated ball mill, 20 parts by weight of the active compound(s) are comminuted with addition of 10 parts by weight of dispersants, 1 part by weight of gelling agent wetters and 70 parts by weight of water or of an organic solvent to give a fine active compound) suspension. Dilution with water gives a stable suspension of the active compound(s), whereby a formulation with 20% (w/w) of active compound(s) is obtained.

I) Capsule Suspensions (CS)
   28 parts of a combination of active compounds, or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 3-10 microns.

2. Products to be Applied Undiluted.

J) Dustable Powders (DP, DS)

5 parts by weight of the active compound(s) are ground finely and mixed intimately with 95 parts by weight of finely divided kaolin. This gives a dustable product having 5% (w/w) of active compound(s).

K) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

L) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:20 to 20:1.

The components of the compositions according to the invention can be used individually or already partially or completely mixed with one another to prepare the composition according to the invention. It is also possible for them to be packaged and used later in time as a composition such as a kit of parts.

In one embodiment of the invention, the kits may include one or more, including all, components that may be used to prepare a subject agrochemical composition. E.g., kits may include one or more herbicide component(s) and/or an adjuvant component and/or another pesticide. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i.e. not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination according to the invention for preparing the composition according to the invention.

In a preferred embodiment of the invention the composition is supplied as a set of two separate containers containing component A and component B, respectively.

In another preferred embodiment the composition is supplied as one container containing component A and component B.

The user applies the composition according to the invention usually from a predosage device, a knapsack sprayer, a spray tank or a spray plane. Here, the composition is made up with water and/or buffer to the desired application concentration, it being possible, if appropriate, to add further auxiliaries, and the ready-to-use spray liquor or the composition according to the invention is thus obtained. Usually, 100 to 1000 liters of the ready-to-use spray liquor are applied per hectare of agricultural useful area, preferably 200 to 500 liters.

The pethoxamid and the picloram and agriculturally acceptable derivatives thereof can be applied jointly or separately, simultaneously or in succession, before, during or after the emergence of the plants i.e. both the useful and/or harmful plants. The order of the application of pethoxamid and the picloram is of minor importance. The only thing that is important is that pethoxamid and the picloram are present simultaneously at the site of action, i.e. are at the same time in contact with or taken up by the plant to be controlled.

The required application rate of pure active compound composition, i.e. pethoxamid and the picloram without formulation auxiliaries depends on the composition of the plant stand, on the development stage of the plants, on the climatic conditions at the site of use and on the application technique. In general, the combined application rate of pethoxamid and the picloram and agriculturally acceptable derivatives thereof is from 0.051 to 3 kg/ha, preferably from 0.06 to 2.5 kg/ha and in particular from 0.1 to 2 kg/ha of active substance (a.s.).

The required application rates of pethoxamid are generally in the range of from 0.05 kg/ha to 2.5 kg/ha and preferably in the range of from 0.1 kg/ha to 2 kg/ha and in particular from 0.4 kg/ha to 1.5 kg/ha of a.s.

The required application rates of picloram and agriculturally acceptable derivatives thereof are generally in the range of from 0.001 kg/ha to 1 kg/ha and preferably in the range of from 0.005 kg/ha to 0.5 kg/ha and in particular from 0.01 kg/ha to 0.1 kg/ha of a.s.

The compositions are applied to the plants mainly by spraying the leaves. Here, the application can be carried out using, for example, water as carrier by customary spraying techniques using spray liquor amounts of from about 100 to 1000 L/ha (for example from 300 to 400 L/ha). The herbicidal compositions may also be applied by the low-volume or the ultra-low-volume method, or in the form of microgranules.

The composition comprising pethoxamid and picloram can be applied pre- or post-emergence. The picloram and agriculturally acceptable derivatives thereof are recommended to be applied post-emergence of the harmful plants to provide a herbicidal effect and pethoxamid recommended for pre-emergence of the harmful plants, However the compositions according to the invention have proved to provide a synergistic herbicidal effect when applied both pre- and post-emergence. This is advantageous since it broadens the time where the combination effectively controls emerging harmful plants. In a preferred embodiment, the compositions are applied early post-emergence.

If the active compounds pethoxamid and picloram are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

Biological Efficacy

The weight ratio of pethoxamid (component A) and the picloram and agriculturally acceptable derivatives thereof (component B) is selected to provide a synergistic pesticidal action, i.e. the compound(s) B be is present in an activity enhancing amount with respect to compound(s) A or vice versa.

A synergistic effect exists whenever the action of a combination of two chemicals is greater than the sum of the action of each of the chemicals alone. Therefore, a synergistic combination is a combination of chemical components having an action that is greater than the sum of the action of each chemical component alone, and a synergistically effective amount is an effective amount of a synergistic combination.

The term "synergistically effective amount" denotes an amount of the composition or of the combinations according to the invention, which is sufficient for providing one or more of the effects: (i) herbicidal activity, (ii) broader activity spectrum, or (iii) extended time frame, with an activity higher than the sum of the individual components. In a preferred embodiment the synergistically effective amount is sufficient for controlling harmful plants e.g. in useful plants while at the same time not resulting in a substantial damage to the treated useful plants. Such an amount may be selected within a broad range and is dependent on various factors, such as the weed species to be controlled, the treated useful plant, the climatic conditions and the specific combination used.

Well-known methods for determining whether synergy exists include the Colby method, the Tammes method and the Wadley method, all of which are described below. Any one of these methods may be used to determine if synergy exists between the compounds A and B.

In the Colby method, also referred to as the Limpels method, the action to be expected E for a given active ingredient combination obeys the so-called Colby formula. According to Colby, the expected action of ingredients A+B using p+q ppm of active ingredient is:

$$E = X + Y - \frac{X \cdot Y}{100}$$

where ppm=milligrams of active ingredient (=a.i.) per liter of spray mixture X=% action by component A using p ppm of active ingredient Y=% action by component B using q ppm of active ingredient. If the ratio R defined as the action actually observed (O) divided by the expected action (E) is >1 then the action of the combination is superadditive, i.e. there is a synergistic effect. For a more detailed description of the Colby formula, see Colby, S. R. "Calculating synergistic and antagonistic responses of herbicide combination," Weeds, Vol. 15, pages 20-22; 1967; see also Limpel et al., Proc. NEWCC 16: 48-53 (1962).

The Tammes method uses a graphic representation to determine whether a synergistic effect exists. See "Isoboles, a graphic representation of synergism in pesticides," Netherlands Journal of Plant Pathology, 70 (1964) p. 73-80.

The Wadley method is based on comparison of an observed ED50 value (i.e. dose of a given compound or combination of compounds providing 50% pest control) obtained from experimental data using the dose response curves and an expected ED50 calculated theoretically from the formula:

$$ED50(A+B)_{exp} = \frac{a+b}{\frac{a}{ED50(A)_{obs}} + \frac{b}{ED50(B)_{obs}}}$$

wherein a and b are the weight ratios of compound A and B in the mixture and $ED50_{obs}$ is the experimentally determined ED50 value obtained using the dose response curves for the individual compounds. The ratio $ED50(A+B)_{expected}/ED50(A+B)_{observed}$ expresses the factor of interaction (F) (synergy factor). In case of synergism, F is >1. The same formula applies when LD50 values are used, i.e. lethal dose, as well as EC50 values, i.e. effective concentration, and LC50 values, i.e. lethal concentration. For a more detailed description of the Wadley method, see Levi et al., EPPO-Bulletin 16, 1986, 651-657.

An alternative approach as mentioned by D. L. Richer (Pesticide Science, 1987, 19, 309-315, especially p. 313) to determine synergy is based on purely observed values rather than observed and theoretical calculated values as used in the previously mentioned methods. In this alternative method the effect of a given rate of the mixture A and B is compared with the effect of the same rate of each of A and B used alone. If synergism exists, the observed effect of the mixture will be greater than the observed effect of either component used alone:

$$E_{obs}(xA+yB) > E_{obs}(x+y)A, \text{ and } > E_{obs}(x+y)B$$

wherein x and y are the quantities of A and B in the mixture.

EXAMPLES

Example 1: The Synergistic Activity of Pethoxamid:Picloram Mixture Against *Galium aparine*

Two field trials are established in commercial fields of winter oilseed rape *Brassica napus*, at sites known to contain natural populations of broad-leaved weeds, including *Galium aparine*. Plots, with a minimum size of 18 m², are arranged with three replicates per treatment.

At each trial, each treatment is applied using a small plot sprayer fitted with flatfan nozzles in a spray volume of 200 l/ha at one of three treatment timings: Timing A—early post-emergence of the oilseed rape, when the crop is at cotyledon to one true leaf stage (BBCH10/11) and pre-emergence of *G. aparine*; Timing B—when the crop has two true leaves (BBCH 12) of the crop and at emergence of *G. aparine* (BBCH09-10). Full application details are recorded, including weather and soil conditions, as well as growth stages and populations of crop and weed species.

Weed control is then assessed by visually estimating the control, as a percentage, relative to the ground cover and vigour of each weed species in the untreated plots. The weed control evaluation is made at 24-27 days, 40-46 days, 54-60 days and 75-81 days after treatment Timing A.

The data is then analysed using the Colby method to determine synergy.

| Entry | Timing | Time | A (pethoxamid, 1200 g a.i/ha) | B (picloram, 23 g a.i/ha) | A + B (O, 1200 + 23 g/ha) | A + B (E, 1200 + 23 g/ha) |
|---|---|---|---|---|---|---|
| 1 | A | 24-27 days | 56.67 | 0 | 83.33 | 56.67 (1.47) |
| 2 | A | 40-46 days | 20 | 0 | 70 | 20 (3.50) |
| 3 | A | 54-60 days | 43.33 | 30 | 83.33 | 60.33 (1.38) |
| 4 | A | 75-81 days | 23.33 | 30 | 92.67 | 43.63 (2.00) |

-continued

| Entry | Timing | Time | A (pethoxamid, 1200 g a.i/ha) | B (picloram, 23 g a.i/ha) | A + B (O, 1200 + 23 g/ha) | A + B (E, 1200 + 23 g/ha) |
|---|---|---|---|---|---|---|
| 5 | B | 24-27 days | 20 | 10 | 30 | 28 (1.07) |
| 6 | B | 40-46 days | 6.67 | 6.67 | 26.67 | 12.89 (2.07) |
| 7 | B | 75-81 days | 50 | 43.33 | 99 | 71.67 (1.38) |

( ) indicates the synergism ratio R, O/E

The invention claimed is:

1. A method for controlling harmful plants comprising exposing the harmful plants to a synergistically effective amount of a combination of, as component A) pethoxamid, and as component B) picloram and agriculturally acceptable derivatives thereof, wherein acceptable derivatives comprise: (a) carboxylic acid derivatives; or, (b) amine derivatives; or (c) combinations of any of these, and wherein components A and B are included in a ratio of about 52:1 (A:B).

2. The method according to claim 1, wherein the harmful plants are present together with useful plants.

3. The method according to claim 1, wherein the combination is applied before, during and/or after emergence of the harmful plants, where component A and component B are applied jointly or separately, simultaneously or in succession.

4. The method according to claim 2, wherein the useful plants are selected among the group consisting of cereals, oilseed rape, corn, soybeans, and cotton.

5. The method according to claim 1, comprising employing a combined application rate of component A and component B of 0.05 to 3 kg/ha.

6. The method according to claim 1, comprising employing from 0.05 to 2.5 kg/ha of component A and from 0.001 to 1 kg/ha of component B, wherein components A and B are included in a ratio of about 52:1 (A:B).

7. The method according to claim 1 wherein the picloram is present, in part or in total, as the dimethylammonium-salt, the triethylammonium salt, the triisopropanolammonium salt, the isoctyl ester (isooctyl) and the potassium salt; and mixtures thereof.

8. A herbicidal composition comprising a combination of, as component A) pethoxamid, and as component B) picloram and agriculturally acceptable derivatives thereof wherein acceptable derivatives comprise: (a) carboxylic acid derivatives; or, (b) amine derivatives; or (c) combinations of any of these wherein components A and B are included in a ratio of about 52:1 (A:B).

9. The composition according to claim 8 comprising at least one solid or liquid carrier and/or one or more surfactants.

10. The composition according to claim 8, wherein component A and component B is present in a form selected from the group consisting of ready-to-use solutions, emulsifiable concentrates, emulsions, suspensions, wettable powders, soluble powders, granules, soluble granules, dispersible granules, microemulsions, microcapsule suspensions, and mixtures thereof.

11. The composition of claim 8 wherein the picloram is present, in part or in total, as the dimethylammonium-salt, the triethylammonium salt, the triisopropanolammonium salt, the isoctyl ester and the potassium salt; and mixtures thereof.

* * * * *